(12) United States Patent
Lieber et al.

(10) Patent No.: US 9,638,717 B2
(45) Date of Patent: May 2, 2017

(54) NANOSCALE SENSORS FOR INTRACELLULAR AND OTHER APPLICATIONS

(71) Applicant: President and Fellows of Harvard College, Cambridge, MA (US)

(72) Inventors: Charles M. Lieber, Lexington, MA (US); Ruixuan Gao, Cambridge, MA (US); Steffen Strehle, Ulm (DE); Xiaojie Duan, Somerville, MA (US); Bozhi Tian, Chicago, IL (US); Itzhaq Cohen-Karni, Cambridge, MA (US); Ping Xie, Needham, MA (US); Quan Qing, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 29 days.

(21) Appl. No.: 14/396,542

(22) PCT Filed: May 2, 2013

(86) PCT No.: PCT/US2013/039228
§ 371 (c)(1),
(2) Date: Oct. 23, 2014

(87) PCT Pub. No.: WO2013/166259
PCT Pub. Date: Nov. 7, 2013

(65) Prior Publication Data
US 2015/0137794 A1    May 21, 2015

Related U.S. Application Data

(60) Provisional application No. 61/642,111, filed on May 3, 2012.

(51) Int. Cl.
*G01R 1/30* (2006.01)
*B82Y 40/00* (2011.01)
(Continued)

(52) U.S. Cl.
CPC ............... *G01R 1/30* (2013.01); *B82Y 40/00* (2013.01); *B82Y 99/00* (2013.01);
(Continued)

(58) Field of Classification Search
CPC .. G01R 1/30; G01R 1/06705; G01R 1/06755; G01R 3/00; G01N 33/48728;
(Continued)

(56) References Cited

U.S. PATENT DOCUMENTS 7,129,554 B2    10/2006    Lieber et al.
7,211,464 B2    5/2007    Lieber et al.
(Continued)

FOREIGN PATENT DOCUMENTS

WO    WO 2007/145701 A2    12/2007
WO    WO 2011/038228 A1    3/2011

OTHER PUBLICATIONS

International Search Report and Written Opinion mailed Aug. 30, 2013 in connection with Application No. PCT/US2013/039228.
(Continued)

*Primary Examiner* — Son Le
*Assistant Examiner* — Akm Zakaria
(74) *Attorney, Agent, or Firm* — Wolf, Greenfield & Sacks, P.C.

(57) ABSTRACT

The present invention generally relates to nanoscale wires for use in sensors and other applications. In various embodiments, a probe comprising a nanotube (or other nanoscale wire) is provided that can be directly inserted into a cell to determine a property of the cell, e.g., an electrical property. In some cases, only the tip of the nanoscale wire is inserted into the cell; this tip may be very small relative to the cell, allowing for very precise study. In some aspects, the tip of the probe is held by a holding member positioned on a substrate, e.g., at an angle, which makes it easier for the
(Continued)

probe to be inserted into the cell. The nanoscale wire may also be connected to electrodes and/or form part of a transistor, such that a property of the nanoscale wire, and thus of the cell, may be determined. Such probes may also be useful for studying other samples besides cells. Other aspects of the invention are generally directed to methods of making or using such probes, kits involving such probes, devices involving such probes, or the like.

11 Claims, 11 Drawing Sheets

(51) Int. Cl.
| G01R 1/067 | (2006.01) |
| G01R 3/00 | (2006.01) |
| H01L 29/772 | (2006.01) |
| H01L 29/41 | (2006.01) |
| H01L 29/423 | (2006.01) |
| B82Y 99/00 | (2011.01) |
| H01L 21/283 | (2006.01) |
| G01N 27/414 | (2006.01) |
| G01N 33/487 | (2006.01) |

(52) U.S. Cl.
CPC ... *G01N 27/4146* (2013.01); *G01N 33/48728* (2013.01); *G01R 1/06705* (2013.01); *G01R 1/06755* (2013.01); *G01R 3/00* (2013.01); *H01L 21/283* (2013.01); *H01L 29/413* (2013.01); *H01L 29/42316* (2013.01); *H01L 29/772* (2013.01)

(58) Field of Classification Search
CPC .... G01N 27/4146; B82Y 99/00; B82Y 40/00; H01L 29/772; H01L 29/42316; H01L 21/283; H01L 29/413
USPC .......................................................... 324/149
See application file for complete search history.

(56) References Cited

U.S. PATENT DOCUMENTS

| 7,301,199 | B2 | 11/2007 | Lieber et al. | |
| 7,875,480 | B2* | 1/2011 | Kamins | B82Y 15/00 |
| | | | | 438/48 |
| 2004/0186459 | A1* | 9/2004 | Shur | B82Y 5/00 |
| | | | | 604/500 |
| 2004/0264064 | A1* | 12/2004 | Sakakima | B82Y 10/00 |
| | | | | 360/322 |
| 2005/0241375 | A1* | 11/2005 | Naughton | B82Y 15/00 |
| | | | | 73/105 |
| 2009/0299213 | A1 | 12/2009 | Patolsky et al. | |
| 2010/0006451 | A1* | 1/2010 | Gordon | G01N 33/5438 |
| | | | | 205/777.5 |
| 2010/0151659 | A1* | 6/2010 | Hong | B82Y 10/00 |
| | | | | 438/478 |
| 2010/0327894 | A1* | 12/2010 | Dang | G01R 1/06738 |
| | | | | 324/755.11 |
| 2012/0267604 | A1 | 10/2012 | Tian et al. | |
| 2014/0080139 | A1 | 3/2014 | Gao et al. | |
| 2014/0184196 | A1 | 7/2014 | Lieber et al. | |

OTHER PUBLICATIONS

International Preliminary Report on Patentability mailed Nov. 13, 2014 in connection with Application No. PCT/US2013/039228.
Duan et al., Intracellular recordings of action potentials by an extracellular nanoscale field-effect transistor. Nat Nanotechnol. Dec. 18, 2011;7(3):174-9. doi: 10.1038/nnano.2011.223.
Duan et al., Supplementary information Intracellular recordings of action potentials by an extracellular nanoscale field-effect transistor. Nat Nanotechnol. Dec. 18, 2011;7(3):174-9. doi: 10.1038/nnano. 2011.223.
Gao et al., Outside looking in: nanotube transistor intracellular sensors. Nano Lett. Jun. 13, 2012;12(6):3329-33. doi: 10.1021/n1301623p. Epub May 22, 2012.
Tian et al., Three-dimensional, flexible nanoscale field-effect transistors as localized bioprobes. Science. Aug. 13, 2010;329(5993):830-4. doi: 10.1126/science.1192033.
Tian et al., Supporting Online Material for Three-dimensional, flexible nanoscale field-effect transistors as localized bioprobes. Science. Aug. 13, 2010;329(5993):830-4. doi: 10.1126/science. 1192033.
U.S. Appl. No. 12/225,142, filed Mar. 11, 2009, Patolsky et al.
U.S. Appl. No. 14/030,170, filed Sep. 18, 2013, Gao et al.
U.S. Appl. No. 13/497,852, filed Jul. 2, 2012, Tian et al.
U.S. Appl. No. 14/124,816, filed Mar. 6, 2014, Lieber et al.
U.S. Appl. No. 14/427,484, filed Mar. 11, 2015, Lieber et al.
U.S. Appl. No. 14/423,340, filed Feb. 23, 2015, Lieber et al.
PCT/US2013/039228, Aug. 30, 2013, International Search Report and Written Opinion.
PCT/US2013/039228, Nov. 13, 2014, International Preliminary Report on Patentability.

* cited by examiner

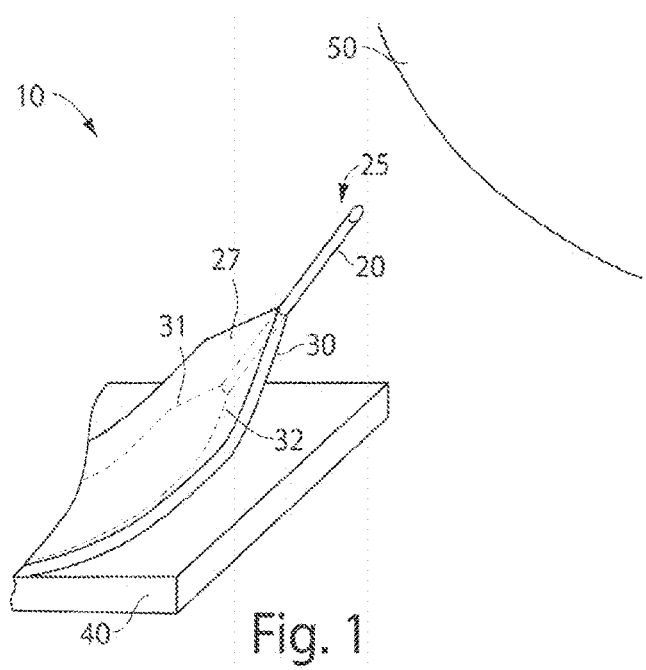

NANOSCALE SENSORS FOR INTRACELLULAR AND OTHER APPLICATIONS

RELATED APPLICATIONS

This application is a national stage filing under 35 U.S.C. §371 of International Patent Application Serial No. PCT/US2013/039228, filed May 2, 2013, entitled "Nanoscale Sensors for Intracellular and Other Applications," by Lieber, et al., which claims the benefit of U.S. Provisional Patent Application Ser. No. 61/642,111, filed May 3, 2012, entitled "Nanoscale Sensors for Intracellular and Other Applications," by Lieber, et al., each incorporated herein by reference in its entirety.

GOVERNMENT FUNDING

This invention was made with government support under Grant No. 5DP1OD003900 awarded by the National Institutes of Health. The U.S. government has certain rights in the invention.

FIELD OF INVENTION

The present invention generally relates to nanoscale wires for use in sensors and other applications.

BACKGROUND

The ideal bio-electronic hybrid interface is expected to require a small and scalable probe to be coupled with cells and tissues. Although current electrophysiological techniques, including patch-clamp micropipettes, microelectrodes, and intracellular micropipettes, have been used, it remains difficult to use such probes to study cells and tissues, e.g., because of the size of such probes. Accordingly, improvements are still needed.

SUMMARY

The present invention generally relates to nanoscale wires for use in sensors and other applications. The subject matter of the present invention involves, in some cases, interrelated products, alternative solutions to a particular problem, and/or a plurality of different uses of one or more systems and/or articles.

In one aspect, the present invention is generally directed to a probe. The probe may be used to probe a cell or other sample, e.g., one that is biological or non-biological. In one set of embodiments, the probe includes a substrate, a holding member positioned on the substrate, a nanoscale wire supported on only one end by the holding member, a first electrode in electrical communication with the nanoscale wire, and a second electrode in electrical communication with the nanoscale wire.

According to another set of embodiments, the probe comprises a substrate, a holding member positioned on the substrate, and a nanoscale wire positioned at an angle away from the substrate by the holding member. In certain embodiments, at least a portion of the nanoscale wire may define a gate of a field effect transistor In still another set of embodiments, the probe may comprise a first electrode, a second electrode, and a third electrode. The probe may also include a first nanoscale wire in electrical communication with the first electrode and the second electrode, and optionally a second nanoscale wire in electrical communication with the first electrode and the third electrode. In some cases, the first electrode, the first nanoscale wire, and the second electrode defines a first field effect transistor. In addition (if applicable), the first electrode, the second nanoscale wire, and the third electrode may define a second field effect transistor.

In yet another set of embodiments, the probe may include a substrate, a holding member positioned on the substrate, a nanoscale wire having a free portion and a held portion, a first electrode physically and/or electrically contacting the electrode portion of the nanoscale wire, and a second electrode physically and/or electrically contacting the electrode portion of the nanoscale wire. In certain embodiments, the holding member holds the nanoscale wire, and in some cases, the held portion may form less than about 50% of the nanoscale wire.

Another aspect of the present invention is generally directed to an article. For example, the article may comprise a non-carbon nanotube, having an interior, positioned such that the interior of the nanotube is in fluidic communication with a cell interior.

Still another aspect of the present invention is generally directed to a method. In one set of embodiments, the method may include acts of depositing a core-shell nanowire on a substrate, patterning a first electrode in electrical communication with the core-shell nanowire, and removing at least a portion of the core of the nanowire, thereby forming a nanotube. In another set of embodiments, the method may include act of removing at least a portion of the core of a core-shell nanowire, e.g., to form a nanotube.

In another aspect, the present invention encompasses methods of making one or more of the embodiments described herein, for example, nanoscale wires used as probes. In still another aspect, the present invention encompasses methods of using one or more of the embodiments described herein, for example, nanoscale wires used as probes.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 1 shows a nanotube probe in accordance with one embodiment of the invention;

DETAILED DESCRIPTION

Figure 2A:
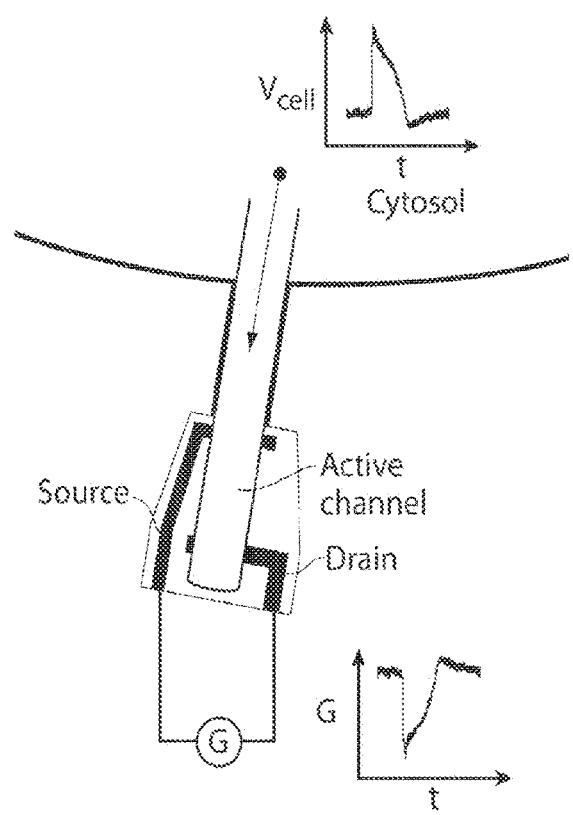
FIGS. 2A-2D illustrate certain FET probes in accordance with various embodiments of the invention.

The present invention generally relates to nanoscale wires for use in sensors and other applications. In various embodiments, a probe comprising a nanotube (or other nanoscale wire) is provided that can be directly inserted into a cell to determine a property of the cell, e.g., an electrical property. In some cases, only the tip of the nanoscale wire is inserted into the cell; this tip may be very small relative to the cell, allowing for very precise study. In some aspects, the tip of the probe is held by a holding member positioned on a substrate, e.g., at an angle, which makes it easier for the probe to be inserted into the cell. The nanoscale wire may also be connected to electrodes and/or form part of a transistor, such that a property of the nanoscale wire, and thus of the cell, may be determined. Such probes may also be useful for studying other samples besides cells. Other aspects of the invention are generally directed to methods of making or using such probes, kits involving such probes, devices involving such probes, or the like.

One example of an embodiment of the invention is now described with respect to FIG. 1. As will be discussed in more detail below, in other embodiments, other configurations may be used as well. In FIG. 1, probe 10 is shown being inserted into cell 50. Although a cell is used here, this is for illustrative purposes only, and in other embodiments, other samples may be probed, biological or nonbiological. Probe 10 includes nanoscale wire 20 and holding member 30 on substrate 40. In this figure, nanoscale wire 20 is a hollow nanotube, having an exterior and an interior, although in other embodiments, nanoscale wire 20 need not be hollow. In addition, only one portion 27 of nanoscale wire 20 is supported by holding member 30, such that some or all of free portion 25 of nanoscale wire 20 can be inserted into cell 50.

Holding member 30 also contains first electrode 31 and second electrode 32, each of which is in electrical communication with the nanoscale wire (although not necessarily in direct electrical communication with each other), and each extending to substrate 40, for example, to one or more electric circuits. As shown in FIG. 1, each of first electrode 31 and second electrode 32 physically contacts nanoscale wire 20 at portion 27, thereby allowing the other portion 25 of the nanoscale wire to remain free for insertion into cell 50. In contrast, in some prior art approaches, there is no free end of a nanoscale wire available for insertion into a cell.

In some embodiments, nanoscale wire 20, first electrode 31, and second electrode 32 may define a field effect transistor ("FET"), e.g., where nanoscale wire 20 defines the gate, first electrode 31 defines the source, and second electrode 32 defines the drain of the FET. The ability of nanoscale wire 20 to act as a gate of a field effect transistor may depend not only on the structure of nanoscale wire 20, but on its environment as well. For example, if nanoscale wire 20 is hollow, then the interior of nanoscale wire 20 may be in fluid and/or electrical communication with the interior of cell 50 once nanoscale wire 20 has been inserted into the cell, such that changes to the interior of nanoscale wire 20, as caused by the cell, can affect the gating abilities of nanoscale wire 20, which can accordingly be determined. Thus, for example, substrate 40 may include electronic components that allow the properties of nanoscale wire 20 (and thus cell 50), to be determined, recorded, transmitted, etc.

The above discussion is a non-limiting example of one embodiment of the present invention that is generally directed to a nanoscale wire used as a probe for a cell or other sample. However, other embodiments are also possible as well. Thus, more generally, various aspects of the invention are directed to various systems and methods for nanoscale wires used as probes. For instance, in certain embodiments, the probe may include a nanoscale wire, a holding member supporting at least a portion of the nanoscale wire, and a substrate that the holding member is positioned on. One, two, or more electrodes may also be present that are in electrical communication with the nanoscale wire.

As mentioned, the probe may include one or more nanoscale wires. In one embodiment, the nanoscale wire is a nanotube. However, in other embodiments, the nanoscale wire may be partially or fully solid (i.e., not hollow). As used herein, a "nanotube" is a nanoscale wire that is hollow, or that has a hollowed-out core or portion thereof, and includes those nanotubes known to those of ordinary skill in the art. For example, the nanotube may be a carbon nanotube or a non-carbon nanotube. If carbon nanotubes are used, they may be single-walled and/or multi-walled, and may be metallic and/or semiconducting in nature. As another example, a nanotube may be created by creating a core/shell nanowire, then etching away at least a portion of the core to leave behind a hollow shell.

In some embodiments, the shell may comprise or consist essentially of a semiconductor. Examples of semiconductors are discussed below. For example, a nanotube may be formed by fabricating a core/shell nanowire, e.g., as discussed herein, then etching away some or all of the core to create a hollow shell. The etching may occur before or after the nanowire is deposited on a substrate. For example, at least about 50%, at least about 60%, at least about 70%, at least about 80%, at least about 90%, or substantially all of the core may be removed. The specific etchant and etching process that is used may depend on the type of material selected for the core. For example, the core may comprise a metal or other material that is easily etchable. As a specific non-limiting example, the core may comprise or consist essentially of germanium and/or metals, which can be etched or otherwise removed without removing the shell (for example, comprising silicon). For instance, the core may be etched using a peroxide (e.g., $H_2O_2$), acetone, a metal etchant (many of which are readily available commercially), or the like. Non-limiting examples of suitable etchable metals are also discussed in detail herein.

In certain embodiments, however, the probe may include one or more nanoscale wires that are not nanotubes. For example, the nanoscale wire may be a "nanowire," i.e., a nanoscale wire that is typically solid (i.e., not hollow). A nanowire may also comprise one or more semiconductors in certain embodiments, e.g., as discussed herein. In addition, other examples of nanoscale wires that may be used in various embodiments include nanorods, inorganic conductive or semiconducting polymers, nanowhiskers, nanoribbons, or the like.

As discussed, in one set of embodiments, the nanoscale wire comprises or consists essentially of a semiconductor. Typically, a semiconductor is an element having semiconductive or semi-metallic properties (i.e., between metallic and non-metallic properties). An example of a semiconductor is silicon. Other non-limiting examples include elemental semiconductors, such as gallium, germanium, diamond (carbon), tin, selenium, tellurium, boron, or phosphorous. In other embodiments, more than one element may be present in the nanoscale wire as the semiconductor, for example, gallium arsenide, gallium nitride, indium phosphide, cadmium selenide, etc. Still other examples include a Group II-VI material (which includes at least one member from Group II of the Periodic Table and at least one member from Group VI, for example, ZnS, ZnSe, ZnSSe, ZnCdS, CdS, or CdSe), or a Group III-V material (which includes at least one member from Group III and at least one member from Group V, for example GaAs, GaP, GaAsP, InAs, InP, AlGaAs, or InAsP).

In certain embodiments, the semiconductor may be undoped or doped (e.g., p-type or n-type). For example, in one set of embodiments, a nanoscale wire may be a p-type semiconductor nanoscale wire or an n-type semiconductor nanoscale wire, and may be used as a component of a transistor such as a field effect transistor ("FET"). For instance, the nanoscale wire may act as the "gate" of a source-gate-drain arrangement of a FET, while metal leads or other conductive pathways (as discussed herein) are used as the source and drain electrodes.

In some embodiments, a dopant or a semiconductor may include mixtures of Group IV elements, for example, a mixture of silicon and carbon, or a mixture of silicon and germanium. In other embodiments, the dopant or the semiconductor may include a mixture of a Group III and a Group V element, for example, BN, BP, BAs, AN, AlP, AlAs, AlSb, GaN, GaP, GaAs, GaSb, InN, InP, InAs, or InSb. Mixtures of these may also be used, for example, a mixture of BN/BP/BAs, or BN/AlP. In other embodiments, the dopants may include alloys of Group III and Group V elements. For example, the alloys may include a mixture of AlGaN, GaPAs, InPAs, GaInN, AlGaInN, GaInAsP, or the like. In other embodiments, the dopants may also include a mixture of Group II and Group VI semiconductors. For example, the semiconductor may include ZnO, ZnS, ZnSe, ZnTe, CdS, CdSe, CdTe, HgS, HgSe, HgTe, BeS, BeSe, BeTe, MgS, MgSe, or the like. Alloys or mixtures of these dopants are also be possible, for example, (ZnCd)Se, or Zn(SSe), or the like. Additionally, alloys of different groups of semiconductors may also be possible, for example, a combination of a Group II-Group VI and a Group III-Group V semiconductor, for example, $(GaAs)_x(ZnS)_{1-x}$. Other examples of dopants may include combinations of Group IV and Group VI elements, such as GeS, GeSe, GeTe, SnS, SnSe, SnTe, PbO, PbS, PbSe, or PbTe. Other semiconductor mixtures may include a combination of a Group I and a Group VII, such as CuF, CuCl, CuBr, CuI, AgF, AgCl, AgBr, AgI, or the like. Other dopant compounds may include different mixtures of these elements, such as $BeSiN_2$, $CaCN_2$, $ZnGeP_2$, $CdSnAs_2$, $ZnSnSb_2$, $CuGeP_3$, $CuSi_2P_3$, $Si_3N_4$, $Ge_3N_4$, $Al_2O_3$, $(Al, Ga, In)_2(S, Se, Te)_3$, $Al_2CO$, $(Cu, Ag)(Al, Ga, In, Tl, Fe)(S, Se, Te)_2$ and the like.

The doping of the semiconductor to produce a p-type or n-type semiconductor may be achieved a variety of doping mechanisms. For example, in one set of embodiments, a doped nanoscale wire may be prepared by incorporating a dopant during catalyzed growth of the nanoscale wire (or portion thereof, e.g., a doped Si shell), e.g., during chemical vapor deposition (CVD). Thus, as non-limiting examples, a p-type nanoscale wire may be prepared by incorporating boron (or other suitable p-type dopants as described herein) during growth of the nanoscale wire, or an n-type nanoscale wire may be prepared by incorporating phosphorous (or other suitable n-type dopants as described herein) during growth of the nanoscale wire. As a specific non-limiting example, a p-type silicon nanowire may be synthesized by flowing both $SiH_4$ (silane) and $B_2H_6$ (diborane) gases in a CVD system.

Other doping techniques may also be used in other embodiments of the invention, for example, bulk-doping, ion implantation, etc. Many such doping techniques that can be used will be familiar to those of ordinary skill in the art, including both bulk doping and surface doping techniques. A bulk-doped article (e.g. an article, or a section or region of an article) is an article for which a dopant is incorporated substantially throughout the crystalline lattice of the article, as opposed to an article in which a dopant is only incorporated in particular regions of the crystal lattice at the atomic scale, for example, only on the surface or exterior. For example, some articles are typically doped after the base material is grown, and thus the dopant only extends a finite distance from the surface or exterior into the interior of the crystalline lattice. It should be understood that "bulk-doped" does not define or reflect a concentration or amount of doping in a semiconductor, nor does it necessarily indicate that the doping is uniform. "Heavily doped" and "lightly doped" are terms the meanings of which are clearly understood by those of ordinary skill in the art. In some cases, one or more regions may comprise a single monolayer of atoms ("delta-doping"). In certain cases, the region may be less than a single monolayer thick (for example, if some of the atoms within the monolayer are absent). As a specific example, the regions may be arranged in a layered structure within the nanoscale wire, and one or more of the regions may be delta-doped or partially delta-doped.

Accordingly, in one set of embodiments, the nanoscale wires may include a heterojunction, e.g., of two regions with dissimilar materials or elements, and/or the same materials or elements but at different ratios or concentrations. The regions of the nanoscale wire may be distinct from each other with minimal cross-contamination, or the composition of the nanoscale wire may vary gradually from one region to the next. The regions may be both longitudinally arranged relative to each other, or radially arranged (e.g., as in a core/shell arrangement) on the nanoscale wire. Each region may be of any size or shape within the wire. The junctions may be, for example, a p/n junction, a p/p junction, an n/n junction, a p/i junction (where i refers to an intrinsic semiconductor), an n/i junction, an i/i junction, or the like. The junction may also be a Schottky junction in some embodiments. The junction may also be, for example, a semiconductor/semiconductor junction, a semiconductor/metal junction, a semiconductor/insulator junction, a metal/metal junction, a metal/insulator junction, an insulator/insulator junction, or the like. The junction may also be a junction of two materials, a doped semiconductor to a doped or an undoped semiconductor, or a junction between regions having different dopant concentrations. The junction may also be a defected region to a perfect single crystal, an amorphous region to a crystal, a crystal to another crystal, an amorphous region to another amorphous region, a defected region to another defected region, an amorphous region to a defected region, or the like. More than two regions may be present, and these regions may have unique compositions or may comprise the same compositions. As one example, a wire may have a first region having a first composition, a second region having a second composition, and a third region having a third composition or the same composition as the first composition. Non-limiting examples of nanoscale wires comprising heterojunctions (including core/shell heterojunctions, longitudinal heterojunctions, etc., as well as combinations thereof) are discussed in U.S. Pat. No. 7,301,199, issued Nov. 27, 2007, entitled "Nanoscale Wires and Related Devices," by Lieber, et al., incorporated herein by reference in its entirety.

In general, a "nanoscale wire" (also known herein as a "nanoscopic-scale wire" or "nanoscopic wire") generally is a wire or other nanoscale object, that at any point along its length, has at least one cross-sectional dimension and, in some embodiments, two orthogonal cross-sectional dimensions (e.g., a diameter) of less than 1 micrometer, less than about 500 nm, less than about 200 nm, less than about 150 nm, less than about 100 nm, less than about 70, less than about 50 nm, less than about 20 nm, less than about 10 nm, less than about 5 nm, than about 2 nm, or less than about 1 nm. In the case of a nanotube, the shell may have any suitable thickness, e.g., less than about 500 nm, less than about 200 nm, less than about 150 nm, less than about 100 nm, less than about 70 nm, less than about 50 nm, less than about 20 nm, less than about 10 nm, less than about 5 nm, than about 2 nm, or less than about 1 nm.

In some embodiments, the nanoscale wire is generally cylindrical. In other embodiments, however, other shapes are possible; for example, the nanoscale wire can be faceted, i.e., the nanoscale wire may have a polygonal cross-section. The cross-section of a nanoscale wire may be of any arbitrary shape, including, but not limited to, circular, square, rectangular, annular, polygonal, or elliptical, and may be a regular or an irregular shape. The nanoscale wire may also be solid or hollow.

In some cases, the nanoscale wire has one dimension that is substantially longer than the other dimensions of the nanoscale wire. For example, the nanoscale may have a longest dimension that is at least about 1 micrometer, at least about 3 micrometers, at least about 5 micrometers, or at least about 10 micrometers or about 20 micrometers in length, or the nanoscale wire may have an aspect ratio (longest dimension to shortest orthogonal dimension) of greater than about 2:1, greater than about 3:1, greater than about 4:1, greater than about 5:1, greater than about 10:1, greater than about 25:1, greater than about 50:1, greater than about 75:1, greater than about 100:1, greater than about 150:1, greater than about 250:1, greater than about 500:1, greater than about 750:1, or greater than about 1000:1 or more in some cases.

In some embodiments, a nanoscale wire may be substantially uniform, or have a variation in average diameter of less than about 30%, less than about 25%, less than about 20%, less than about 15%, less than about 10%, or less than about 5%. For example, the nanoscale wires may be grown from substantially uniform nanoclusters or particles, e.g., colloid particles. See, e.g., U.S. Pat. No. 7,301,199, issued Nov. 27, 2007, entitled "Nanoscale Wires and Related Devices," by Lieber, et al., incorporated herein by reference in its entirety.

In some embodiments, the nanoscale wires used herein are individual or free-standing nanoscale wires. For example, an "individual" or a "free-standing" nanoscale wire may, at some point in its life, not be attached to another article, for example, with another nanoscale wire, or the free-standing nanoscale wire may be in solution. This is in contrast to nanoscale features etched onto the surface of a substrate, e.g., a silicon wafer, in which the nanoscale features are never removed from the surface of the substrate as a free-standing article. This is also in contrast to conductive portions of articles which differ from surrounding material only by having been altered chemically or physically, in situ, i.e., where a portion of a uniform article is made different from its surroundings by selective doping, etching, etc. An "individual" or a "free-standing" nanoscale wire is one that can be (but need not be) removed from the location where it is made, as an individual article, and transported to a different location and combined with different components to make a functional device such as those described herein and those that would be contemplated by those of ordinary skill in the art upon reading this disclosure.

In one set of embodiments, the nanoscale wire is formed from a single crystal, for example, a single crystal nanoscale wire comprising a semiconductor. A single crystal item may be formed via covalent bonding, ionic bonding, or the like, and/or combinations thereof. While such a single crystal item may include defects in the crystal in some cases, the single crystal item is distinguished from an item that includes one or more crystals, not ionically or covalently bonded, but merely in close proximity to one another.

In some embodiments, a nanoscale wire has a conductivity of or of similar magnitude to any semiconductor or any metal. The nanoscale wire may be formed of suitable materials, e.g., semiconductors, metals, etc., as well as any suitable combinations thereof. In some cases, the nanoscale wire will have the ability to pass electrical charge, for example, being electrically conductive. For example, the nanoscale wire may have a relatively low resistivity, e.g., less than about $10^{-3}$ Ohm m ($\Omega$m), less than about $10^{-4}$ Ohm m, less than about $10^{-6}$ Ohm m, or less than about $10^{-7}$ Ohm m. The nanoscale wire may, in some embodiments, have a conductance of at least about 1 microsiemens, at least about 3 microsiemens, at least about 10 microsiemens, at least about 30 microsiemens, or at least about 100 microsiemens.

In one aspect, the nanoscale wire (e.g., a nanotube or a nanowire) may be held at an angle away from the surface of the substrate, for example, by a suitable holding member. In some embodiments, the holding member comprises a polymer, such as a photoresist. For example, the photoresist can be chosen for its ability to react to light to become substantially insoluble (or substantially soluble, in some cases) to a photoresist developer. For instance, photoresists that may be used within a polymeric construct include, but are not limited to, SU-8, S1805, LOR 3A, poly(methyl methacrylate), poly(methyl glutarimide), phenol formaldehyde resin (diazonaphthoquinone/novolac), diazonaphthoquinone (DNQ), Hoechst AZ 4620, Hoechst AZ 4562, Shipley 1400-17, Shipley 1400-27, Shipley 1400-37, or the like. These and many other photoresists are available commercially. In some embodiments, one or more portions of the photoresist can be exposed to light (visible, UV, etc.), electrons, ions, X-rays, etc. (e.g., projected onto the photoresist), and the exposed portions may be etched away (e.g., using suitable etchants, plasma, etc.) to produce the pattern.

In some embodiments, only a portion of the nanoscale wire is held by the holding member, e.g., such that only one end of the nanoscale wire is supported by the holding member. For example, the nanoscale wire may comprise a free portion (not in physical contact with the holding member) and a held portion (in physical contact with the holding member), such that the free portion is at least about 10%, at least about 20%, at least about 30%, at least about 40%, at least about 50%, at least about 60%, at least about 70%, at least about 80%, or at least about 90% of the nanoscale wire. In addition, more than one free portion and/or held portion may be present in some embodiments.

The holding member may hold the nanoscale wire at any suitable angle away from the substrate. For example, the angle can be about 10°, about 20°, about 30°, about 40°, about 50°, about 60°, about 70°, about 80°, or about 90° (i.e., vertically positioned relative to the substrate). If more than one nanoscale wire is held by the holding member, the nanoscale wires can be held at the same or different angles.

The holding member may be angled away from the substrate, in one set of embodiments, by depositing two or more dissimilar metals on the holding member that may warp or bend, thereby causing the holding member to warp away from the substrate. In some (but not all) embodiments, the metals can also be used for one or more electrodes, e.g., as discussed herein. As a specific non-limiting example, chromium and palladium may be layered or deposited on each other in such a way that stresses occur between the metals, thereby causing warping or bending. As another non-limiting example, copper and chromium may be layered or deposited on each other to cause warping or bending. The amount and type of stress can also be controlled, e.g., by controlling the thicknesses of the layers. For example, relatively thinner layers may be used to increase the amount of warping that occurs.

As specific examples, the thickness of a metal can be less than about 5 micrometers, less than about 4 micrometers, less than about 3 micrometers, less than about 2 micrometers, less than about 1 micrometer, less than about 700 nm, less than about 600 nm, less than about 500 nm, less than about 300 nm, less than about 200 nm, less than about 100 nm, less than about 80 nm, less than about 50 nm, less than about 30 nm, less than about 10 nm, less than about 5 nm, less than about 2 nm, etc. The thickness of the layer may also be at least about 10 nm, at least about 20 nm, at least about 40 nm, at least about 60 nm, at least about 80 nm, or at least about 100 nm. For example, the thickness of a metal can be between about 40 nm and about 100 nm, between about 50 nm and about 80 nm. In addition, the thicknesses of the two or more metals may independently be the same or different.

Furthermore, in some cases, longer lengths of metals may also be used to control the amount of bending or warping, in addition to and/or instead of controlling the thicknesses of the metals. For example, by using longer lengths in the holding member, larger angles and/or heights of the nanoscale wire, relative to the substrate, may be achieved. For example, the effect of a relatively small deflection in two dissimilar metals may be geometrically increased due to longer lengths of metals that are bent or warped, even if at any one location, the amount of deflection or stress is relatively small.

Without wishing to be bound by any theory, it is believed that layering metals having a difference in stress (e.g., film stress) with respect to each other may, in some cases, cause stresses within the metal, which can cause bending or warping as the metals seek to relieve the stresses. For example, a first layer having a first film stress deposited on a second layer having a second film stress greater than the first film stress may cause bending or warping towards the direction of the second layer. In certain embodiments, the deposition of stressed metals may occur at one or more specific locations, e.g., to cause specific warpings to occur, e.g., at certain places, which may be used to cause the holding member to be deformed into a particular shape or configuration. For example, a "line" of such mismatches can be used to cause an intentional bending or folding along the line of the holding member.

As mentioned, such metals also can be used to form one or more electrodes, although this is not a requirement. However, in various embodiments, one or more electrodes may be positioned in electrical and/or physical communication with the nanoscale wires, e.g., to create a conductive pathway from the substrate to the nanoscale wire. Thus, the electrode can be patterned to be in direct physical contact the nanoscale wire and/or there may be other materials between the electrode and the nanoscale wire that allow electrical communication to occur. Metals may be used for the electrode due to their high conductance, e.g., such that changes within electrical properties obtained from the conductive pathway may be related to changes in properties of the nanoscale wire, rather than changes in properties of the conductive pathway. However, in other embodiments, other types of electrode materials are used, in addition or instead of metals.

A wide variety of metals may be used in various embodiments of the invention, for example in an electrode. As non-limiting examples, the metals may include one or more of aluminum, gold, silver, copper, molybdenum, tantalum, titanium, nickel, tungsten, chromium, palladium, as well as any combinations of these and/or other metals. In some cases, the metal may be chosen to be one that is readily introduced, e.g., using techniques compatible with lithographic techniques. For example, in one set of embodiments, lithographic techniques such as e-beam lithography, photolithography, X-ray lithography, extreme ultraviolet lithography, ion projection lithography, etc. can be used to pattern or deposit one or more metals on a substrate. Additional processing steps can also be used to define or register the electrode in some cases. Thus, for example, the thickness of an electrode may be less than about 5 micrometers, less than about 4 micrometers, less than about 3 micrometers, less than about 2 micrometers, less than about 1 micrometer, less than about 700 nm, less than about 600 nm, less than about 500 nm, less than about 300 nm, less than about 200 nm, less than about 100 nm, less than about 80 nm, less than about 50 nm, less than about 30 nm, less than about 10 nm, less than about 5 nm, less than about 2 nm, etc. The thickness of the electrode may also be at least about 10 nm, at least about 20 nm, at least about 40 nm, at least about 60 nm, at least about 80 nm, or at least about 100 nm. For example, the thickness of an electrode may be between about 40 nm and about 100 nm, between about 50 nm and about 80 nm.

In some embodiments, more than one metal may be used within an electrode (e.g., as previously discussed). The metals can be deposited in different regions or alloyed together, or in some cases, the metals may be layered on top of each other, e.g., layered on top of each other using various lithographic techniques. For example, a second metal may be deposited on a first metal, and in some cases, a third metal may be deposited on the second metal, etc. Additional layers of metal (e.g., fourth, fifth, sixth, etc.) can also be used in some embodiments. The metals may all be different, or in some cases, some of the metals (e.g., the first and third metals) may be the same. Each layer may independently be of any suitable thickness or dimension, e.g., of the dimensions described above, and the thicknesses of the various layers may independently be the same or different.

In some embodiments, two or more electrodes are used, e.g., in electrical communication with a nanoscale wire (although not necessarily in direct electrical communication with each other). For example, two electrodes and a nanoscale wire may define a transistor such as a field effect transistor, e.g., where the nanoscale wire defines the gate and the electrodes define the source and the drain. As mentioned, the environment in and/or around the nanoscale wire can affect the ability of the nanoscale wire to function as a gate. For instance, if the nanoscale wire is a nanotube having an interior which is positioned to be in fluid and/or electrical communication with a cell or other sample, then the gating functions of the nanoscale wire may be a function, at least in part, of the cell or other sample, such that the field effect transistor can be used as a probe.

The holding member is positioned on a substrate in certain embodiments. The substrate may be chosen to be one that can be used for lithographic techniques such as e-beam lithography or photolithography, or other lithographic techniques including those discussed herein. For example, the substrate can comprise or consist essentially of a semiconductor material such as silicon, although other substrate materials (e.g., a metal) can also be used. Typically, the substrate is one that is substantially planar, e.g., so that polymers, metals, and the like can be patterned on the substrate. In addition, the substrate typically contains other electronic components, for example, in electrical communication with one or more electrodes, or otherwise forming part of an electrical circuit. Examples include, but are not limited to, transistors such as field effect transistors, resistors, capacitors, inductors, diodes, integrated circuits, etc. In some cases, some of these may also comprise nanoscale wires.

In some embodiments, a portion of the substrate can be oxidized, e.g., forming $SiO_2$ and/or $Si_3N_4$ on a portion of the substrate, which may facilitate subsequent addition of materials (metals, polymers, etc.) to the substrate. In some cases, the oxidized portion may form a layer of material on the substrate, e.g., having a thickness of less than about 5 micrometers, less than about 4 micrometers, less than about 3 micrometers, less than about 2 micrometers, less than about 1 micrometer, less than about 900 nm, less than about 800 nm, less than about 700 nm, less than about 600 nm, less than about 500 nm, less than about 400 nm, less than about 300 nm, less than about 200 nm, less than about 100 nm, etc. In some cases, the substrate can include a sacrificial material that may then be removed, e.g., to cause the holding member to hold the nanoscale wire at an angle away from the substrate. As noted, in some cases, portions of the holding member and/or electrodes may be deposited such that, upon removal of the sacrificial material, stresses within the holding member may cause warping or bending such that the holding member holds the nanoscale wire at an angle away from the substrate.

In one set of embodiments, for example, at least a portion of the sacrificial material can be exposed to an etchant able to remove the sacrificial material. For example, if the sacrificial material is a metal such as nickel, a suitable etchant (for example, a metal etchant such as a nickel etchant, acetone, etc.) may be used to remove the sacrificial metal. Many such etchants may be readily obtained commercially.

In some aspects, the nanoscale wire is used to determine a property of the environment in and/or around the nanoscale wire, e.g., a chemical property, an electrical property, a physical property, etc. Such determination may be qualitative and/or quantitative. For example, in one set of embodiments, the nanoscale wire may be responsive to an electrical property such as voltage. For instance, the nanoscale wire can exhibit a voltage sensitivity of at least about 5 microsiemens/V; by determining the conductivity of a nanoscale wire, the voltage surrounding the nanoscale wire may thus be determined. In other embodiments, the voltage sensitivity may be at least about 10 microsiemens/V, at least about 30 microsiemens/V, at least about 50 microsiemens/V, or at least about 100 microsiemens/V. Other examples of electrical properties that can be determined include resistance, resistivity, conductance, conductivity, impendence, or the like.

As another example, the nanoscale wire may be used to determine a chemical property of the environment in and/or around the nanoscale wire. For example, an electrical property of the nanoscale wire can be affected by a chemical environment surrounding the nanoscale wire, and the electrical property can be thereby determined to determine the chemical environment. As a specific non-limiting example, the nanoscale wires may be sensitive to pH or hydrogen ions. Further non-limiting examples of such nanoscale wires are discussed in U.S. Pat. No. 7,129,554, filed Oct. 31, 2006, entitled "Nanosensors," by Lieber, et al., incorporated herein by reference in its entirety.

As a non-limiting example, the nanoscale wire may have the inherent ability to bind to an analyte indicative of a chemical property of the environment in and/or around the nanoscale wire (e.g., hydrogen ions for pH, or concentration for an analyte of interest), and/or the nanoscale wire may be partially or fully functionalized, i.e. comprising surface functional moieties, to which an analyte is able to bind, thereby causing a determinable property change to the nanoscale wire, e.g., a change to the resistivity or impedance of the nanoscale wire. The binding of the analyte can be specific or non-specific. Functional moieties may include simple groups, selected from the groups including, but not limited to, —OH, —CHO, —COOH, —$SO_3H$, —CN, —$NH_2$, —SH, —COSH, —COOR, halide; biomolecular entities including, but not limited to, amino acids, proteins, sugars, DNA, antibodies, antigens, and enzymes; grafted polymer chains with chain length less than the diameter of the nanowire core, selected from a group of polymers including, but not limited to, polyamide, polyester, polyimide, polyacrylic; a shell of material comprising, for example, metals, semiconductors, and insulators, which may be a metallic element, an oxide, an sulfide, a nitride, a selenide, a polymer and a polymer gel.

In some embodiments, a reaction entity may be bound to a surface of the nanoscale wire (e.g., an exterior and/or an interior surface), and/or positioned in relation to the nanoscale wire such that the analyte can be determined by determining a change in a property of the nanoscale wire. Thus, as specific non-limiting examples, one or more reaction entities may be positioned inside and/or outside of a nanotube. The determination may be quantitative and/or qualitative, depending on the application. The term "reaction entity" refers to any entity that can interact with an analyte in such a manner to cause a detectable change in a property (such as an electrical property) of a nanoscale wire. The reaction entity may enhance the interaction between the nanowire and the analyte, or generate a new chemical species that has a higher affinity to the nanowire, or to enrich the analyte around the nanowire. The reaction entity can comprise a binding partner to which the analyte binds. The reaction entity, when a binding partner, can comprise a specific binding partner of the analyte. For example, the reaction entity may be a nucleic acid, an antibody, a sugar, a carbohydrate or a protein. Alternatively, the reaction entity may be a polymer, catalyst, or a quantum dot. A reaction entity that is a catalyst can catalyze a reaction involving the analyte, resulting in a product that causes a detectable change in the nanowire, e.g. via binding to an auxiliary binding partner of the product electrically coupled to the nanowire. Another exemplary reaction entity is a reactant that reacts with the analyte, producing a product that can cause a detectable change in the nanowire. The reaction entity can comprise a shell on the nanowire, e.g. a shell of a polymer that recognizes molecules in, e.g., a gaseous sample, causing a change in conductivity of the polymer which, in turn, causes a detectable change in the nanowire.

The term "binding partner" refers to a molecule that can undergo binding with a particular analyte, or "binding partner" thereof, and includes specific, semi-specific, and non-specific binding partners as known to those of ordinary skill in the art. The term "specifically binds," when referring to a binding partner (e.g., protein, nucleic acid, antibody, etc.), refers to a reaction that is determinative of the presence and/or identity of one or other member of the binding pair in a mixture of heterogeneous molecules (e.g., proteins and other biologics). Thus, for example, in the case of a receptor/ligand binding pair the ligand would specifically and/or preferentially select its receptor from a complex mixture of molecules, or vice versa. An enzyme would specifically bind to its substrate, a nucleic acid would specifically bind to its complement, an antibody would specifically bind to its antigen. Other examples include, nucleic acids that specifically bind (hybridize) to their complement, antibodies specifically bind to their antigen, and the like. The binding may be by one or more of a variety of mechanisms including, but not limited to ionic interactions, and/or covalent interactions, and/or hydrophobic interactions, and/or van der Waals interactions, etc.

As previously discussed, more than one nanoscale wire may be used in certain embodiments. For example, the probe may comprise 2, 3, 4, 5, 6, 7, 8, 9, 10, or more nanoscale wires. The nanoscale wires may each independently be the same or different. For example, each of the nanoscale wires may be a nanotube, each of the nanoscale wires may be a nanowire, or some of the nanoscale wires may be nanotubes and some may be nanowires.

Figure 5A:
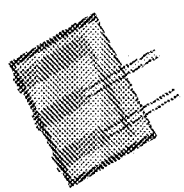
FIGS. 5A-5E illustrate probes comprising more than one nanotube, in yet other embodiments of the invention.

In some embodiments, some or all of the nanoscale wires may be used as gates of field effect transistors, and in certain cases, some or all of the nanoscale wire may share one or more electrodes. For example, as is shown in FIG. 5A, a probe having two nanoscale wires each acting as gates in a field effect transistor is shown, with three electrodes such that one electrode acts as a source to the two nanoscale wires and the other two electrodes act as drains to the two nanoscale wires. In yet other embodiments, there may be two, three, four, five, etc. field effect transistors present. In some cases, the field effect transistors may share one or more electrodes, although in other cases, there may be no shared electrodes.

The nanoscale wire can be inserted into a cell using any suitable technique, for example, manually, or using micromanipulation techniques known to those of ordinary skill in the art. In other embodiments, however, a cell may be pushed or otherwise moved so as to be in contact with the nanoscale wire. At least a portion of the nanoscale wire may be inserted internally of a cell in certain embodiments, e.g., to determine a property internally of the cell, although in other embodiments, the nanoscale wire need not be inserted into the cell (e.g., to determine a property externally of the cell). In addition, it should be noted that while cells are discussed above, this is by way of each of explanation only, and in other embodiments, other types of samples can be determined, qualitatively and/or quantitatively, instead of and/or in addition to cells. Such samples may be biological or non-biological, depending on the application. For example, biological tissues or electronic circuits can be studied in some cases. Thus, in various embodiments, any suitable sample which is desired to be probed with a nanoscale wire as is discussed herein may be studied.

The following documents are incorporated herein by reference in their entireties: U.S. Pat. No. 7,211,464, issued May 1, 2007, entitled "Doped Elongated Semiconductors, Growing Such Semiconductors, Devices Including Such Semiconductors, and Fabricating Such Devices," by Lieber, et al.; U.S. Pat. No. 7,301,199, issued Nov. 27, 2007, entitled "Nanoscale Wires and Related Devices," by Lieber, et al.; and International Patent Application No. PCT/US2010/050199, filed Sep. 24, 2010, entitled "Bent Nanowires and Related Probing of Species," by Tian, et al., published as WO 2011/038228 on Mar. 31, 2011.

The following examples are intended to illustrate certain embodiments of the present invention, but do not exemplify the full scope of the invention.

Example 1

Nanowire-based field-effect transistors (NWFETs), including devices with planar and three-dimensional (3D) configurations, have been explored as detectors for extra- and intracellular recording due to their small size and high sensitivities. Particularly, NWFETs have shown advantage for cellular recording due to their small size, large input impedance, and high signal to noise ratio. See, for example, International Patent Application No. PCT/US2010/050199, filed Sep. 24, 2010, entitled "Bent Nanowires and Related Probing of Species," by Tian, et al., published as WO 2011/038228 on Mar. 31, 2011, incorporated herein by reference. The present examples illustrate the synthesis, fabrication, and characterization of new nanoprobes based on an active silicon nanotube transistor ("ANTT") that allows for high-resolution intracellular recording. While silicon nanotubes are discussed in these examples, this is by way of example only, and other types of nanoscale wires may also be used, e.g., as previously described. In the nanoprobes discussed here, the source/drain (S/D) contacts to the silicon nanotube were fabricated on one end, passivated from external solution, and then time-dependent changes in potential were recorded from the opposite nanotube end via the solution filling the tube. Measurements of conductance versus water-gate potential in aqueous solution showed that the probe was selectively gated by potential changes within the nanotube, thus demonstrating the basic operating principles. Studies interfacing the probe with spontaneously beating cardiomyocytes yielded stable intracellular action potentials similar to those reported by other electrophysiological techniques. In addition, the straightforward fabrication of the devices was exploited to prepare multiple nanotube structures at the end of single probes, which allowed multiplexed recording of intracellular action potentials from single cells, and multiplexed arrays of single device probes. These studies open up unique opportunities in a variety of areas, e.g., multisite recordings from individual cells through cellular networks.

This example demonstrates a field-effect transistor based probe having a single semiconductor nanotube (although probes with more than one nanotube are discussed below). The underlying principle of the active nanotube transistor intracellular probe (FIG. 2A) involves the fabrication of S/D contacts to one end of a silicon or other semiconductor nanotube and electrical isolation of these S/D contacts from surrounding medium such that the solution filling the interior of the nanotube can gate the transistor, and the variation of interior electrochemical potential can then be recorded as a change in device conductance. Hence, if the free end of the probe is inserted into the interior of an electrogenic cell, the time-dependent changes associated with an action potential spike will give rise to a time-varying conductance signal that maps the intracellular action potential. However, if a similarly configured solid silicon (or other semiconductor) nanowire is inserted into the cell, no signal (or a much poorer signal) would be observed. For the p-type silicon nanotubes as used in these examples, a positive change of intracellular potential yielded a negative change in device conductance (FIG. 2A), although the conductance could be quantitatively converted to potential using water-gate calibration or other measurements.

The probes were fabricated on the $Si_3N_4$ surface of silicon substrates (100 nm thermal $SiO_2$, 200 nm $Si_3N_4$, n-type, 0.005 V cm, Nova Electronic Materials). A Ni sacrificial layer (80 nm) was first defined by electron beam lithography (EBL) and thermal evaporation (TE). The substrate was then coated with SU-8 resist (2000.5, MicroChem Corp.), on which the Ge/Si core/shell nanowires were deposited by either of two methods: (1) nanowires suspended in isopropyl alcohol were deposited from solution; or (2) nanowires were directly contact-printed as described previously. See, e.g., International Patent Application No. PCT/US2007/008540, filed Apr. 6, 2007, entitled "Nanoscale Wire Methods and Devices," by Nam, et al., published as WO 2007/145701 on Dec. 21, 2007, incorporated herein by reference. After definition of the bottom SU-8 support layer by EBL, source/drain (S/D) metal contacts were defined by EBL and metalized by thermal evaporation of Cr/Pd/Cr (1.5/75/50 nm). Typically, the S/D contact separation was 0.5-1 micrometers and the free end of the nanowire extended 3-4 micrometers from the source contact. The top SU-8 layer was subsequently defined by EBL for passivation. Etching of the Ni sacrificial layer (1.5 h) in nickel etchant (TFB, Transene Company, Inc.) and the Ge core of the core/shell nanowire (65° C., 30-60 min) in hydrogen peroxide ($H_2O_2$, 30%, Sigma) yielded the probes.

Figure 2B:
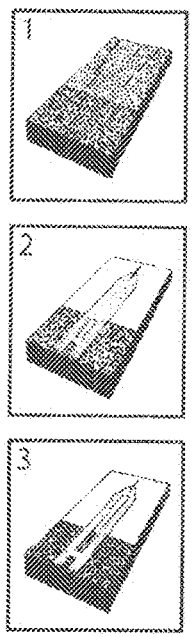

The fabrication of the probes was carried out in several steps briefly illustrated in FIG. 2B. First, Ge/Si core/shell NWs were synthesized by nanocluster catalyzed vapor-liquid-solid (VLS) growth of Ge NWs followed by p-type Si shell deposition as described previously. See, e.g., U.S. Pat. No. 7,211,464, issued May 1, 2007, entitled "Doped Elongated Semiconductors, Growing Such Semiconductors, Devices Including Such Semiconductors, and Fabricating Such Devices," by Lieber, et al., incorporated herein by reference. Briefly, 50 or 15 nm diameter gold nanoparticles (Ted Pella) were dispersed on $Si/SiO_2$ substrates (Nova Electronic Materials). The Ge core growth was carried out using $GeH_4$ (20-30 sccm, 10% in $H_2$) and $H_2$ (200 sccm) for 30 min at a total pressure of 300-400 Torr and temperature of 270-310° C. The p-type Si shell (about 25 nm in thickness) was subsequently grown on the 50 nm Ge core by uncatalyzed decomposition of $SiH_4$ (1 sccm) and $B_2H_6$ (10 sccm, 100 ppm in $H_2$) at a total pressure of 20 Torr and temperature of 475° C. for 30 min. It was noted that the p-type Si shell (15-20 nm) growth on the 15 nm Ge core was carried out at a reduced deposition rate: 3 sccm $SiH_4$, 15 sccm $B_2H_6$ (100 ppm in $H_2$) and 50 sccm $H_2$ at a total pressure of 9 Torr and temperature of 450° C. for 40 min. A final annealing step at 600° C. for 1.5 h under vacuum ($2.8 \times 10^{-3}$ Torr) gave crystalline Ge/Si core/shell nanowires.

Figure 2C:
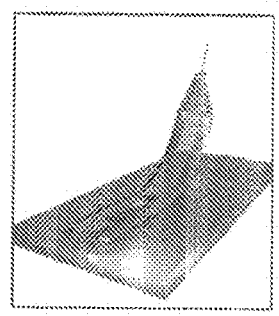

The Ge/Si NWs were dispersed from isopropyl alcohol or contact printed onto a prebaked SU-8 layer, which was initially deposited on a sacrificial nickel relief layer. After defining the lower SU-8 passivation/isolation layer by electron beam lithography (EBL), S/D metal contacts (Cr/Pd/Cr, 1.5/75/50 nm) followed by an upper SU-8 passivation/isolation layer were patterned by EBL. Etching the nickel sacrificial layer and Ge core of the Ge/Si NW yielded the p-type Si ANTT probe (FIG. 2C). Scanning electron microscopy (SEM) images of the probes (FIG. 2D) confirmed the basic fabrication strategy and showed the nanotube structure. Comparison of SEM images of the device before and after the Ge core etching (FIG. 7) showed the open tip and a "bright-to-dark" change in image contrast along the length of the structure that is indicative of an open nanotube from the tip through to the S/D metal contacts. The "bend-up" angles, typically 40 to 60° and height, usually 15-30 micrometers in these examples, were controlled by changing the length of the stressed bimetallic S/D arms.

Figure 2D:
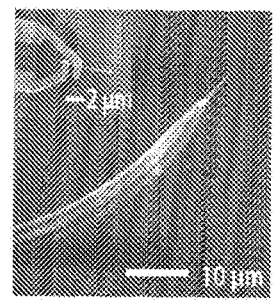

FIG. 2A shows a schematic view of a probe inserted into a cell and recording an intracellular action potential ($V_{cell}$ vs. time, t) as a conductance (G) change in the active FET region between S/D contacts. The sensitivity to voltage changes from the external extracellular environment was effectively eliminated by SU-8 passivation of the nanotube region around the S/D contacts. The nanotube is shown as a half-cylinder for clarity. FIG. 2B shows an overview of the steps used for probe fabrication: (1) Transfer of Ge/Si core/shell nanowires (Ge/Si NWs) to a SU-8 layer that was deposited and prebaked on a sacrificial layer. (2) Registration of positions of Ge/Si NWs and definition of the bottom SU-8 layer. (3) Definition of S/D metal contacts followed by the top SU-8 passivation layer. Final etching of the sacrificial layer and Ge NW core yielded the probe. FIG. 2C shows a schematic of the completed probe following release from the substrate. FIG. 2D is a scanning electron microscopy (SEM) image of the probe. Scale bar is 10 micrometers. The inset is a zoom of the probe tip from the dashed box. The scale bar is 100 nm.

Figure 7A:
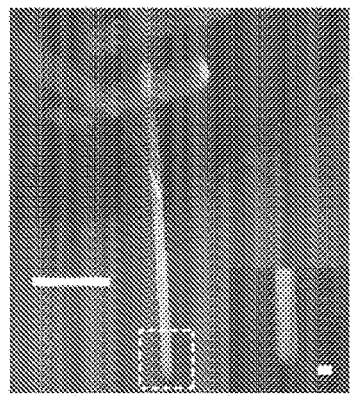
FIGS. 7A-7C illustrate SEM images of a probe before and after etching, in accordance with another embodiment of the invention.
Figure 7B:
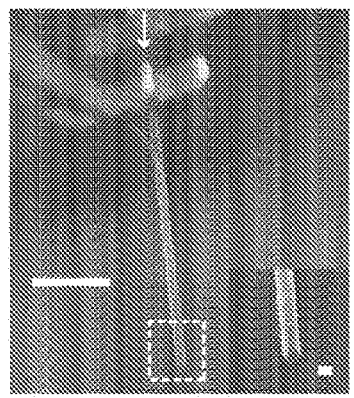
Figure 7C:
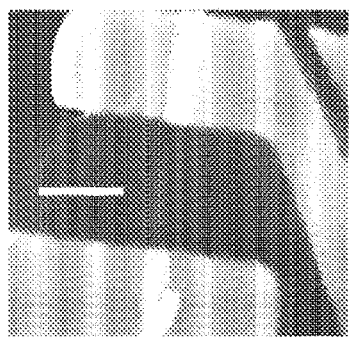

FIG. 7 shows SEM images of a probe before and after Ge core nanowire etching. FIG. 7A is an SEM image of a probe before etching the Ge core of the Ge/Si core/shell nanowire. The scale bar is 1 micrometer. The inset is a zoom of the probe tip from the dashed box. The scale bar is 100 nm. FIG. 7B is an SEM image of the same probe after etching of Ge nanowire core. The scale bar is 1 micrometer. The inset is a zoom of the probe tip from the dashed box showing the tube structure. The scale bar is 100 nm. FIG. 7C is a zoomed top view of the S/D contact region of the probe in FIG. 7B (indicated by the arrow). The scale bar is 500 nm. The "light-dark-light" contrast variation demonstrates that the tube structure (light, Si nanotube walls; dark, hollow core) continues from tip to S/D region of the device.

Example 2

Figure 3A:
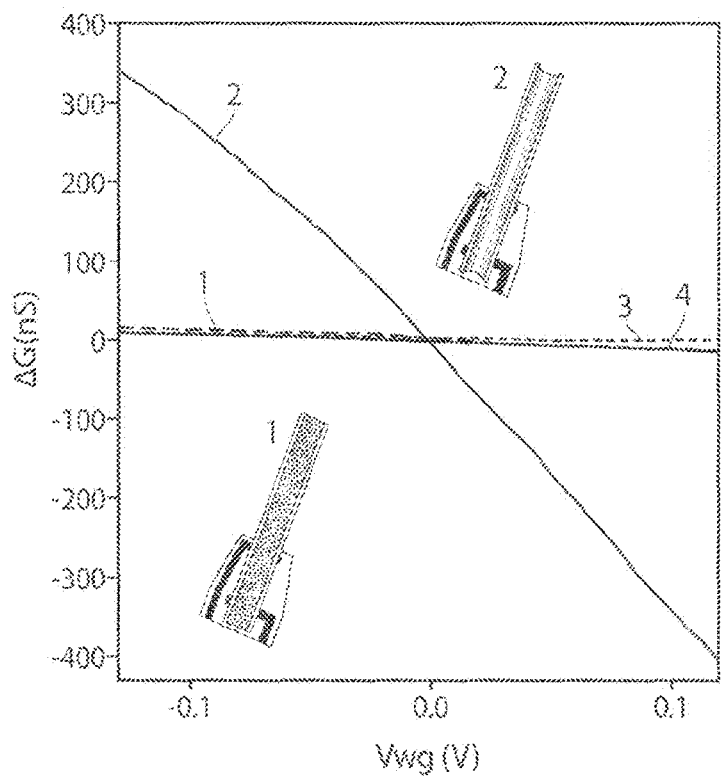
FIGS. 3A-3B illustrate the characterization of various FET probes in certain embodiments of the invention.

This example illustrates the electrical properties of probe structures fabricated as discussed in Example 1 in aqueous solution before and after etching the Ge NW cores. Prior to Ge-etching, conductance (G) versus water-gate potential ($V_{wg}$) data showed only a small change with a sensitivity of ~0.10 microsiemens/V (FIG. 3A). Notably, after etching the Ge core to form the probe device the water-gate data exhibited a 30× sensitivity increase to 3.0 microsiemens/V. The device sensitivity (S/V) was defined as S/D conductance change in response to gate voltage ($V_{wg}$) applied by Ag/AgCl reference electrode. $V_{wg}$ was typically swept at a rate of 80 mV/s from −0.4 V to +0.4 V. The S/D current, driven by 100 mV source voltage, was amplified by a current preamplifier (1211, DL Instruments) at sensitivity of $10^{-6}$ or $10^{-7}$ A/V, filtered (0-3 kHz, CyberAmp 380, Molecular Devices, Inc.) and digitized at 50-250 kHz sampling rate (Axon Digidata 1440A Data Acquisition System, Molecular Devices, Inc.).

These results were consistent with the increased gate coupling afforded by solution access to the Si-nanotube interior. To rule out the possibility that the Ge-etching process degraded the SU-8 passivation, control experiments were performed on a Si/Si intrinsic-core/p-shell NW structure, where the shell was similar to the Ge/Si core/shell NWs used to make devices. Significantly, the Si/Si control device with SU-8 passivated S/D contacts showed similar sensitivity to the Ge/Si device and little or no sensitivity change following the same etching conditions used to remove Ge and yield the device. Taken together these results showed that (1) the top/bottom SU-8 passivation effectively isolated the FET channel from external solution potential changes, and (2) the probe structure had good sensitivity to potential changes coupled through solution in the nanotube interior.

The following experiments show the capability of the device discussed above to detect chemical changes in pH sensing experiments. Measurements of the G as a function of stepwise increasing pH showed a systematic increase with the increasing negative charge on the $SiO_2$ surface of the p-type nanotube interior. These data plotted as change in potential versus solution pH (FIG. 3B) yielded a device pH sensitivity of up to 37 mV/pH. This value was consistent with previous results reported for Si NW devices. Measurements made before and after closing the nanotube device end with SU-8 (inset, FIG. 3B) confirmed that this change was due to pH detection from the solution inside the nanotube, as no variation in G was observed after blocking solution exchange. These results showed the potential of the probe to detect chemical and biochemical changes as previously demonstrated by nanowire FET sensors.

Figure 3B:
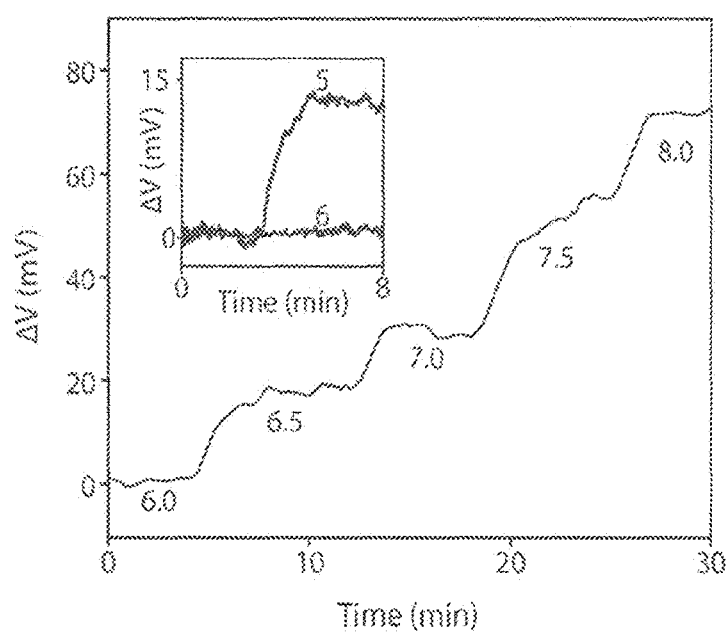

These data are illustrated in FIG. 3. FIG. 3A shows the change of conductance, $\Delta G$, versus water-gate potential, $V_{wg}$, prior to (1) and after (2) $H_2O_2$ etching of the Ge NW core. Plots (3) and (4) correspond to $\Delta G$ versus $V_{wg}$ for a Si/Si intrinsic-core/p-shell NW device before and after, respectively, etching using the same conditions as for the Ge/Si NW structure. All measurements were made in 1× phosphate-buffered saline (1×PBS) with a Ag/AgCl reference gate electrode. Insets show schematics of the device prior to (1) and after (2) $H_2O_2$ etching of the Ge NW core. FIG. 3B shows the change in potential, $\Delta V$, in response to step changes in solution pH. The potential values were calculated from the measured device conductance using the measured water-gate sensitivity of 2.0 microsiemens/V. The inset shows $\Delta V$ as the pH is increased stepwise from 7.0 to 8.0 for the device (5) and the same device after closing the tip with SU-8 resist to prevent solution access (6).

Example 3

This example illustrates the recording intracellular action potential with probes similar to those discussed above using spontaneously firing chicken cardiomyocytes. In these experiments, ANTT probes relieved from the surface (e.g., FIG. 2D) were modified with a phospholipid layer, cardiomyocytes were cultured on flexible sheets of polydimethylsiloxane (PDMS) as described previously, and then the PDMS/cell sheet was moved to orient a single cell over a probe tip with an optical microscope. See, e.g., International Patent Application No. PCT/US2010/050199, filed Sep. 24, 2010, entitled "Bent Nanowires and Related Probing of Species," by Tian, et al., published as WO 2011/038228 on Mar. 31, 2011, incorporated herein by reference.

Embryonic chicken cardiomyocytes on PDMS were prepared using published protocols. Before intracellular recording, probe chips were incubated with lipid vesicles of 1,2-dimyristoyl-sn-glycero-3-phosphocholine (DMPC, Avanti Polar Lipids Inc.) containing 1% 1-myristoyl-2-{12-[(7-nitro-2-1,3-benzoxadiazol-4-yl)amino]dodecanoyl}-sn-glycero-3-phosphocholine (NBD-lipid, Avanti Polar Lipids Inc.) as a fluorescence reporter. The recordings were carried out in 1× Tyrode solution (pH 7.3) at 37° C. using a 100 mV DC source voltage for the devices. The S/D current was converted to voltage with a current preamplifier, low-pass filtered and digitized. A pulled glass micropipette was used for manipulation of the cardiomyocytes/PDMS sheet.

After contact with the cell, regularly spaced spikes were initially observed with a frequency of 1.8 Hz (FIG. 4A) and correlated with cell beating. These peaks detected initially after contact had widths of ~0.7 ms and amplitudes up to 10 mV that were consistent with extracellular cardiomyocyte action potentials reported previously.

Notably, over a period of about 100 seconds following contact between the probe tip and the PDMS-supported cell the recorded periodic signals change substantially (FIG. 4B) with an increase in amplitude and duration to 40-50 mV and about 200 ms respectively. Over a period of several minutes the peak amplitude continued to increase until stable periodic peaks were observed (FIG. 4C) with amplitude and duration of about 80 mV and 200 ms, respectively. The peak duration and shape were similar to values reported for cardiomyocyte intracellular action potentials, and thus these data can be associated with intracellular action potential recording by the probe. Indeed, closer examination of a representative steady-state recorded peak (FIG. 4D) showed five phases that could be associated with (1) resting state, (2) rapid depolarization, (3) plateau, (4) rapid repolarization, and (5) hyperpolarization. It is also noted that experiments carried out with a smaller inner/outer diameter (15/50 nm) probes (FIG. 8) showed similar intracellular action potential peaks with about 75 mV amplitude, consistent with the size-scaling predicted for the related BIT-FET.

Figure 4A:
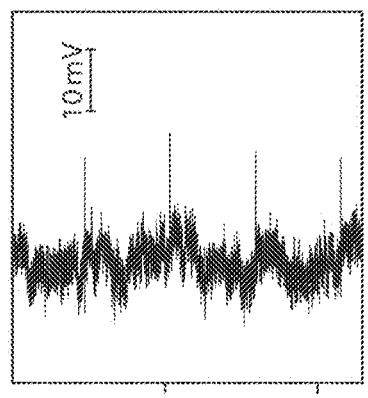
FIGS. 4A-4D illustrate intracellular potential recordings of cells determined using some embodiments of the invention.
Figure 4B:
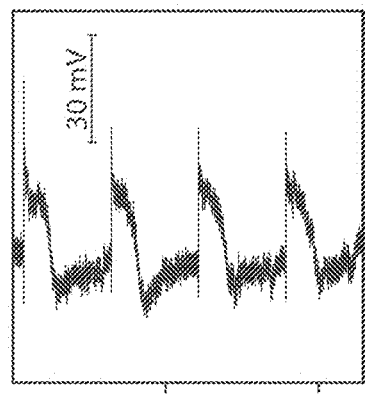
Figure 4C:
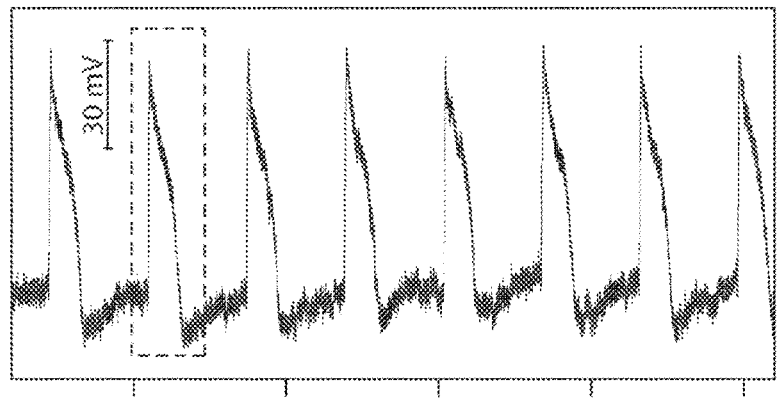
Figure 4D:
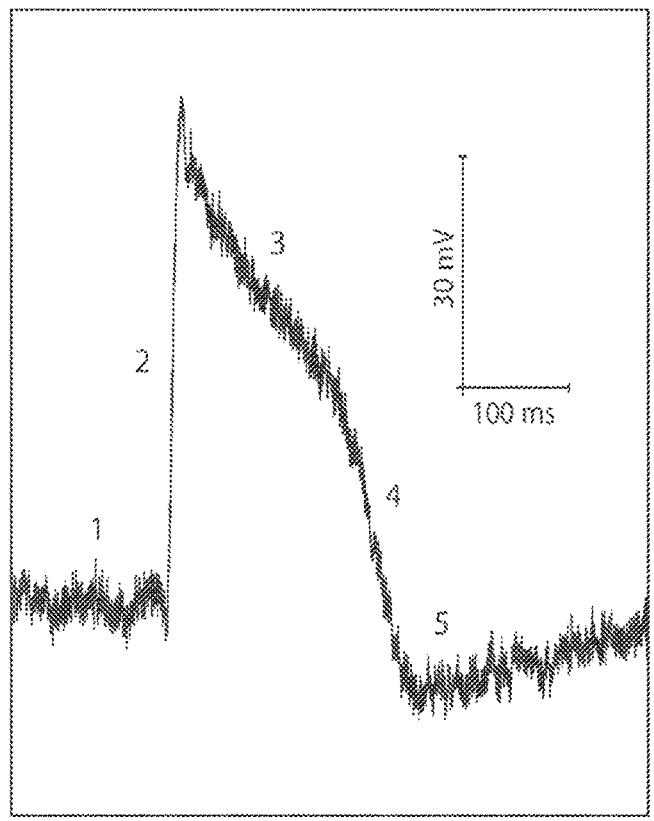

FIG. 4A shows representative potential vs. time data recorded immediately following contact between the probe and a single cardiomyocyte. FIG. 4B shows representative potential vs. time data recorded about 100 s following contact between the probe and a single cardiomyocyte and the trace in FIG. 4A. FIG. 4C shows stable potential vs. time data recorded about 5 min following the trace in FIG. 4B. The tick marks in FIGS. 4A-4C correspond to 1 s. FIG. 4D is a zoom of the single intracellular action potential peak in the trace in FIG. 4C, highlighted with the dashed box. The five characteristic phases of the action potential peak, denoted by 1-5, are discussed above. In all the traces, the recorded device conductance was calibrated with the measured water-gate sensitivity to yield the plotted voltage signal.

Figure 8:
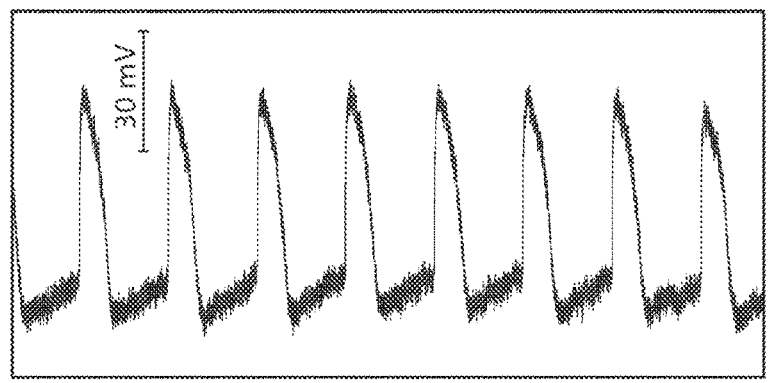
FIG. 8 illustrates intracellular recording of a cell in yet another embodiment of the invention.

FIG. 8 shows intracellular recording with small diameter probe, and stable intracellular action potential recordings from a spontaneously-beating cardiomyocytes. The amplitude was about 75 mV; tick marks corresponded to 1 s. The dimensions of the silicon nanotube tip were controlled by growth time and Au catalyst size during nanowire synthesis, and have approximately 15 nm inner and 50 nm outer diameters. The spontaneously beating cells were cultured on thin PDMS sheets and then brought into gentle contact with the device.

Example 4

This example illustrates multiplexed recording with probes similar to those discussed above, including (1) multiple ANTTs on a single probe and (2) arrays of ANTT probes. First, probes with two ANTTs were fabricated as shown schematically in FIG. 5A. Steps in fabrication involved contact-printing of the Ge/Si core/shell NWs to produce parallel NWs, and the use of a common source contact for both devices; the remainder of the fabrication process was similar to that described above. See, e.g., International Patent Application No. PCT/US2007/008540, filed Apr. 6, 2007, entitled "Nanoscale Wire Methods and Devices," by Nam, et al., published as WO 2007/145701 on Dec. 21, 2007, incorporated herein by reference.

Figure 5B:
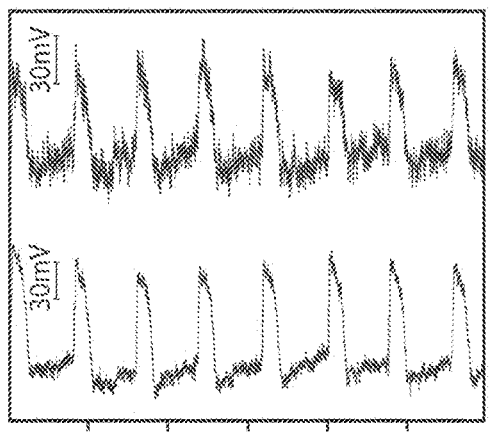

A representative SEM image (FIG. 5A) showed two nanotubes on a single 3D probe with a nanotube tip-to-tip separation of about 7.6 micrometers. Notably, measurements made from two such devices on a single probe following contact with one beating cardiomyocyte (FIG. 5B) demonstrated regular intracellular action potential peaks from both devices. At steady-state the peaks recorded by both nanotubes exhibited potential changes of about 80 mV, which was consistent with intracellular action potentials and results reported recently for a two-element BIT-FET. Examination of the data recorded by both nanotubes showed that the noise in both channels was not correlated, and there was no significant electrical crosstalk between the dual-device/single-probe configuration even when recording from the same cell.

Figure 5C:
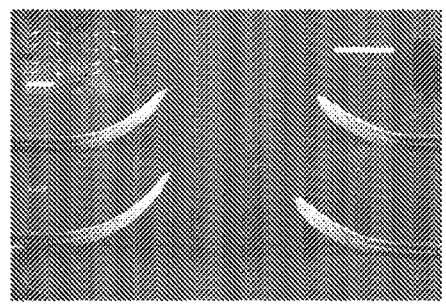

As another example, a 4×4 array of single ANTT probes, with an average probe spacing of 80 micrometers, was fabricated from contact-printed Ge/Si NWs (FIG. 5C). Denser probe arrays could be fabricated by varying the printing conditions.

These examples thus demonstrate the design, synthesis, fabrication and testing of new hollow needle-shaped nanoprobes based on an active silicon nanotube transistor or ANTT. Measurements of conductance versus water-gate potential in aqueous solution have shown that the ANTT probe was selectively gated by potential change within the silicon nanotube, thus demonstrating the basic operating principles. Studies interfacing ANTT probes with spontaneously beating cardiomyocytes demonstrated the recording of stable full-amplitude intracellular action potentials, and moreover, showed that full-amplitude action potentials could be recorded with small inner tube diameters, e.g., 15 nm. In addition, the straightforward fabrication of ANTT devices was exploited to prepare multiple ANTTs at the end of single probes, which allowed multiplexed recording of full-amplitude intracellular action potentials from single cells, and multiplexed arrays of single ANTTs. These studies open up unique opportunities for multisite recordings from individual cells through cellular networks, including the potential for intracellular chemical sensing through modification of the inner tube surface, as is discussed herein.

Example 5

Figure 5D:
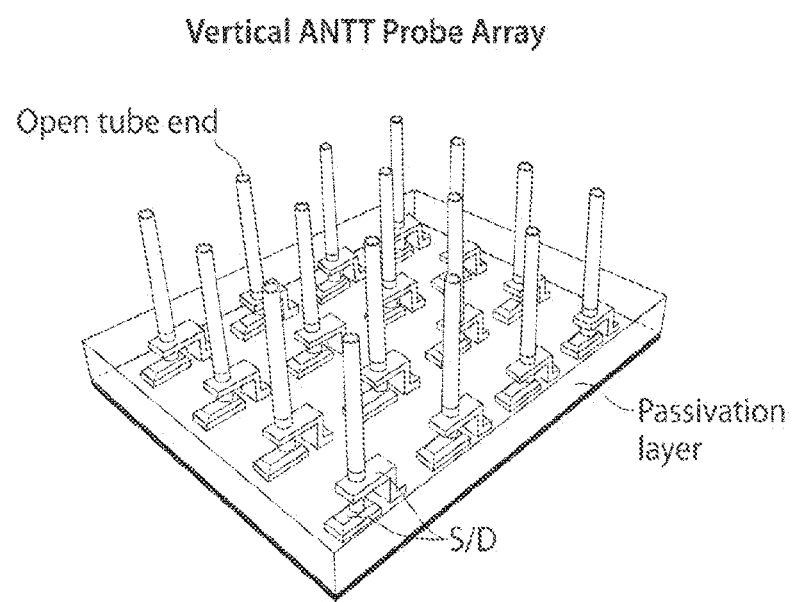
Figure 5E:
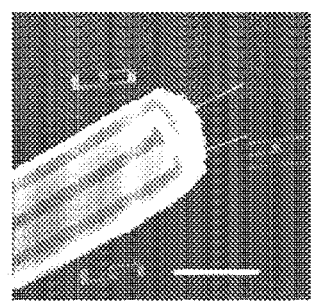
Figure 6A:
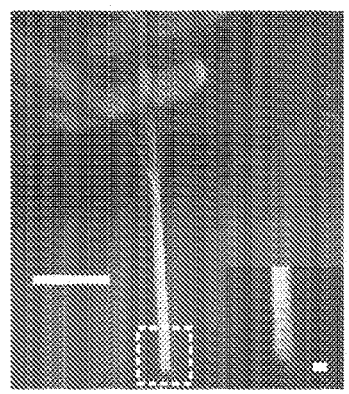
FIGS. 6A-6C illustrate SEM images of a probe in one embodiment of the invention.
Figure 6B:
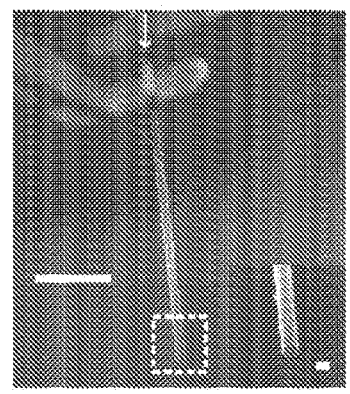
Figure 6C:
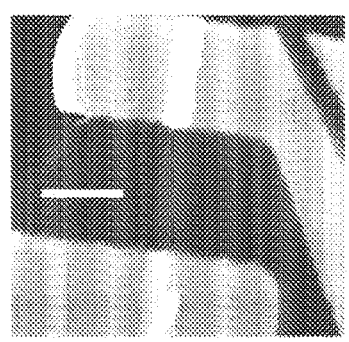

This example shows on chip-based fabrication of an active tube arrays for further integration. The source and drain contacts are defined vertically to SiNT arrays, and fully passivated in dielectrics (FIG. 5D). This strategy involves epitaxial growth of approximately vertical Ge/Si NWs to produce high-density ANTT probe arrays (FIG. 5D).

In this example, vertical silicon nanotube arrays are grown vertical or close to vertical to the substrate, to which two metal contacts (source and drain) are defined, to form an active field effect transistor (FET) region. The active FET region is passivated from the outside so that the gating potential is conducted to the FET region only through the open end of the nanotube.

The structure can be formed by depositing a thin Ge layer (e.g., on the order of hundreds of nanometers) on a substrate (silicon, silicon oxide or other substrates) in a chemical vapor deposition system (CVD). Gold (Au) nanoparticles (NPs) can be defined on top of the substrate. These can either be dispersed from commercially available AuNPs for a random array, or the AuNPs can be defined by e-beam lithography and thermoevaporation for a regular and predefined array. Next, a Ge core can be grown epitaxially to the substrate via vapor-liquid-solid (VLS) growth mechanism in CVD, and the Si shells (e.g., doped) can be grown via uncatalyzed deposition in CVD.

The first metal contact may be deposited on the epitaxially grown Ge/Si core/shell nanowires (NWs), and an insulating layer (for example, silicon oxide, aluminum oxide, hafnium oxide and other types of dielectrics) can be deposited on top of the first metal contact. Similarly, the second metal contact can be deposited on the epitaxially grown Ge/Si core/shell NWs. The second metal contact may be the same or different from the first metal contact.

A passivation layer (e.g., SU-8) can be deposited (e.g., via spin-coating) to be of a desirable height (e.g., so that the S/D contacts are buried). A protection layer (e.g., of a resist) can then be deposited to be a desirable height. For instance, the protection layer may be deposited to be thicker than the passivation layer. This height can be used to define the final height of the probe.

The tip of the NWs can be etched away, e.g., using suitable etching techniques such as those described herein, including all the metal/dielectrics remnants from the previous steps. Similarly, the Ge core can be etched away, e.g., using a hydrogen peroxide aqueous solution, to produce the final probe.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article, comprising:
   a non-carbon nanotube, having an interior, positioned such that the interior of the nanotube is in fluidic communication with a cell interior, and
   a holding member supporting at least a portion of the non-carbon nanotube, wherein the holding member supports only one end of the non-carbon nanotube,
   wherein at least a portion of the non-carbon nanotube defines a gate of a field effect transistor.

2. The article of claim 1, further comprising:
   a substrate,
   wherein the holding member is positioned on the substrate, and
   wherein the non-carbon nanotube is supported on only one end by the holding member;
   a first electrode in electrical communication with the non-carbon nanotube; and
   a second electrode in electrical communication with the non-carbon nanotube.

3. The article of claim 2, wherein the substrate comprises silicon.

4. The article of claim 2, wherein the holding member holds the non-carbon nanotube at an angle away from the substrate.

5. The article of claim 1, wherein the holding member comprises a polymer and/or a photoresist.

6. The article of claim 1, wherein the non-carbon nanotube comprises a semiconductor.

7. The article of claim 6, wherein the non-carbon nanotube comprises silicon.

8. The article of claim 2, wherein the first electrode comprises chromium and/or palladium, and/or copper.

9. The article of claim 2, wherein the first electrode comprises a first metal and a second metal different from the first metal.

10. The article of claim 1, wherein the non-carbon nanotube has a free portion and a held portion, wherein the holding member physically contacts the non-carbon nanotube at the held portion.

11. The article of claim 10, wherein the held portion forms less than about 50% of the non-carbon nanotube.

* * * * *

UNITED STATES PATENT AND TRADEMARK OFFICE
CERTIFICATE OF CORRECTION

PATENT NO. : 9,638,717 B2
APPLICATION NO. : 14/396542
DATED : May 2, 2017
INVENTOR(S) : Charles M. Lieber et al.

It is certified that error appears in the above-identified patent and that said Letters Patent is hereby corrected as shown below:

In the Specification

At Column 1, Lines 19-22, (approx.) the paragraph under the heading GOVERNMENT FUNDING should be replaced with the following paragraph:
This invention was made with government support under OD003900 awarded by the National Institutes of Health. The government has certain rights in the invention.

Signed and Sealed this
Fifth Day of May, 2020

Andrei Iancu
*Director of the United States Patent and Trademark Office*